United States Patent [19]
Winslow

[11] Patent Number: 5,968,098
[45] Date of Patent: *Oct. 19, 1999

[54] APPARATUS FOR FUSING ADJACENT BONE STRUCTURES

[75] Inventor: Charles J. Winslow, Walnut Creek, Calif.

[73] Assignee: Surgical Dynamics, Inc., Norwalk, Conn.

[*] Notice: This patent issued on a continued prosecution application filed under 37 CFR 1.53(d), and is subject to the twenty year patent term provisions of 35 U.S.C. 154(a)(2).

[21] Appl. No.: 08/734,911

[22] Filed: Oct. 22, 1996

[51] Int. Cl.⁶ ................................. A61F 2/28; A61F 2/44
[52] U.S. Cl. ............................... 623/17; 623/16; 623/18; 606/60; 606/61; 606/72; 606/73
[58] Field of Search ................................. 623/16, 17, 18; 606/60, 61, 72, 73

[56] References Cited

U.S. PATENT DOCUMENTS

| | | |
|---|---|---|
| 3,486,505 | 12/1969 | Morrison . |
| 3,719,186 | 3/1973 | Merig, Jr. . |
| 3,848,601 | 11/1974 | Ma et al. . |
| 3,905,047 | 9/1975 | Long . |
| 3,916,907 | 11/1975 | Peterson . |
| 4,177,524 | 12/1979 | Grell et al. . |
| 4,484,570 | 11/1984 | Sutter et al. . |
| 4,501,269 | 2/1985 | Bagby . |
| 4,537,185 | 8/1985 | Stednitz . |
| 4,545,374 | 10/1985 | Jacobson . |
| 4,573,448 | 3/1986 | Kambin . |
| 4,677,972 | 7/1987 | Tornier . |
| 4,743,256 | 5/1988 | Brantigan . |
| 4,772,287 | 9/1988 | Ray et al. . |
| 4,820,305 | 4/1989 | Harms et al. ............................. 623/16 |
| 4,834,757 | 5/1989 | Brantigan ................................. 623/17 |
| 4,877,020 | 10/1989 | Vich . |
| 4,878,915 | 11/1989 | Brantigan . |
| 4,927,421 | 5/1990 | Goble et al. . |
| 4,936,848 | 6/1990 | Bagby ....................................... 623/17 |
| 4,950,270 | 8/1990 | Bowman et al. ......................... 606/72 |
| 4,961,740 | 10/1990 | Ray et al. ................................. 606/61 |
| 5,015,247 | 5/1991 | Michelson ................................ 606/61 |
| 5,015,255 | 5/1991 | Kuslich ..................................... 623/17 |

(List continued on next page.)

FOREIGN PATENT DOCUMENTS

| | | |
|---|---|---|
| 0307241 | 3/1989 | European Pat. Off. . |
| 0551187 | 7/1993 | European Pat. Off. . |
| 0716840 | 6/1996 | European Pat. Off. . |
| 0732093 | 9/1996 | European Pat. Off. . |
| 0734703 | 10/1996 | European Pat. Off. . |

(List continued on next page.)

OTHER PUBLICATIONS

Actualites Vertebrales, La Herni Discale Cervicale, No. 2, Avril 1994, pp. 1–11.

Kiyoshi Kaneda and Isao Yamamoto, "Spinal Instrumentation Surgery In Lumbar and Lumbosacral Spine," *The Improvement of Medicine,* vol. 147, No. 14, Dec. 31, 1988.

Hiroshi Yamamoto, "Spinal Instrumentation For Lumbar Spine Segmental Transverse Wiring For Spondylolysis and Pedicular Screw–Spinal Plate For Spondylolisthesis," *The Improvement of Medicine,* vol. 145, No. 1, Apr. 2, 1988.

(List continued on next page.)

*Primary Examiner*—David J. Isabella
*Assistant Examiner*—Choon P. Koh

[57] ABSTRACT

An apparatus for facilitating the fusion of adjacent bone structures includes an implant member configured for insertion within a space defined between adjacent bone structures. The implant member includes an entry end portion and a trailing end portion and defines a longitudinal axis. The implant member includes at least a longitudinal portion having a generally elliptical cross-sectional dimension with a major cross-sectional dimension greater than a minor cross-sectional dimension. The apparatus is particularly contemplated for fusion of adjacent vertebrae.

28 Claims, 13 Drawing Sheets

U.S. PATENT DOCUMENTS

| | | | |
|---|---|---|---|
| 5,026,373 | 6/1991 | Ray et al. | 606/61 |
| 5,055,104 | 10/1991 | Ray | 606/61 |
| 5,062,845 | 11/1991 | Kuslich et al. | 606/80 |
| 5,192,327 | 3/1993 | Brantigan . | |
| 5,300,076 | 4/1994 | Leriche | 606/73 |
| 5,313,962 | 5/1994 | Obenchain | 128/898 |
| 5,395,317 | 3/1995 | Kambin | 604/51 |
| 5,423,816 | 6/1995 | Lin | 606/61 |
| 5,423,817 | 6/1995 | Lin | 606/61 |
| 5,425,772 | 6/1995 | Brantigan | 623/17 |
| 5,431,658 | 7/1995 | Moskovich | 606/99 |
| 5,439,464 | 8/1995 | Shapiro | 606/83 |
| 5,443,514 | 8/1995 | Steffee | 623/17 |
| 5,458,638 | 10/1995 | Kuslich et al. | 623/17 |
| 5,522,899 | 6/1996 | Michelson . | |
| 5,534,031 | 7/1996 | Matsuzaki et al. . | |
| 5,554,191 | 9/1996 | Lahille et al. . | |
| 5,562,736 | 10/1996 | Ray et al. . | |
| 5,571,109 | 11/1996 | Bertagnoli . | |
| 5,571,189 | 11/1996 | Kuslich . | |
| 5,571,192 | 11/1996 | Schönhöffer . | |
| 5,593,409 | 1/1997 | Michelson | 623/17 X |
| 5,609,636 | 3/1997 | Kohrs et al. | 623/17 |

FOREIGN PATENT DOCUMENTS

| | | |
|---|---|---|
| 2295729 | 12/1974 | France . |
| 5729348 | 2/1982 | Japan . |
| 5878653 | 5/1983 | Japan . |
| 61-135652 | 6/1986 | Japan . |
| 62-164458 | 7/1987 | Japan . |
| 4633654 | 2/1988 | Japan . |
| 1502402 | 8/1989 | Japan . |
| 1314560 | 12/1989 | Japan . |
| 8707827 | 12/1987 | WIPO . |
| 8912431 | 12/1989 | WIPO . |
| 9106261 | 5/1991 | WIPO . |
| 9417759 | 8/1994 | WIPO . |
| 9608205 | 3/1996 | WIPO . |

OTHER PUBLICATIONS

Kenichiro Shibata, Masayoshi Oga, Kazuo Hayashi, Yoichi Sugioka, "A New Contrivance of Anterior Spinal Fusion in Cervical Spine", *Orthopaedic and Traumatic Surgery*, vol. 35, No. 3, pp. 811–813, 1987.

Haruo Tsuji, "Anterior Body Fusion of Lumber Spine Hernia," *Operation*, vol. 41, No. 11, pp. 1803–1811, 1987.

Hirotugo Oda, Shinya Kawai, Tetsuro Murakami, et al., "Osteoplastic Hemi/Bilateral Partial Laminectomy of Lumbar Spinal Hernia," *Operation*, vol. 41, No. 11, pp. 1785–1791, 1987.

Teiji Yano, et al., "Treatment of Spondylolisthesis By Posterior Fusion With Bone Grafting To Neutral Arch Defect," *Clinical Orthopaedic Surgery*, vol. 17, No. 4, pp. 394–399, 1982.

Toshihiko Yamane, et al., "A Case Report of Multiple Lumbar Spondylolyses With Spondylolisthesis," *Clinical Orthopaedic Surgery*, vol. 23, No. 3, pp. 311–314, 1988.

M. Maeshiro, K. Otani, K. Shibasaki, S. Nakai, K. Nemoto, M. Yoshida, "Posterior Fracture–Dislocation of the Thoracic Spine; Two Case Report," *Orthopedic surgery*, vol. 39, No. 9 pp. 1373–1377, 1988–9.

Kunio Takaoka, "Clinical Application of Ceramic Implants in Orthopedics Surgery," *Medicina Philosophics*, vol. 4, No. 7 pp. 546–552, 1985.

Y. Yamano, Y. Mikawa, R. Watanabe, et al., "Anterior Body Fusion of Lumbar Degenerative Spondylolisthesis," *Journal of the Western Japanese Reserach Society For Spine*, vol. 13, pp. 46–50.

Dual Chisel and Its Bank Bones (Skimud Subkortikale Bones) For Posterior Lumbar Interbody Fusion—In Order To Simplify and Regularize the Surgical Procedure, *Orthopaedic Surgery*, vol. 11, pp. 150–153.

Vertebral body Distraction System (Caspar), "Orthopaedic Surgery", vol. 11, pp. 135–139.

Takayoshi Ueda, et al., "Instrumentation Surgery of Lumbar Interbody Fusion," *Central Japan Journal of Orthopaedic & Traumatic Surgery*, pp. 87–89.

Haruo Tsuji, et al., "Development and Clinical Application of Artificial Intervertebral Disc For Cervical Disc Lesions," *Central Japan Journal of Orthopaedic & Traumatic Surgery*, pp. 1505–1506.

Jose M. Otero Vich, "Anterior Cervical Interbody Fusion With Threaded Cylindrical Bone", *J. Neurosurg.*, 63:750–753, 1985.

Norman W. Hoover, "Methods of Lumbar Fusion", *The Journal of Bone and Joint Surgery*, vol. 50–A, No. 1, Jan. 1968, pp. 194–210.

Benjamin R. Wiltberger, "Intervertebral Body Fusion By the Use of Posterior Bone Dowel", pp. 69–79.

Parviz Kambin et al., "Percutaneous Lateral Discectomy of the Lumbar Spine", *Clinical Orthopaedics*, Apr. 1983, vol. 174, pp. 127–131.

Guy M. Sava et al., "Posterior Lumbar Interbody Fusion Made Simple", Neurological Surgery Associates of Cincinnati, Inc.

Cage CH: Lumbar Spacing Cages, *Scientix* .

Actualites Vertebrales, La Herni Discale Cervicale, No. 2, Avril 1994, pp. 1–11.

Kiyoshi Kaneda and Isao Yamamoto, "Spinal Instrumentation Surgery In Lumbar and Lumbosacral Spine," *The Improvement of Medicine*, vol. 147, No. 14, Dec. 31, 1988.

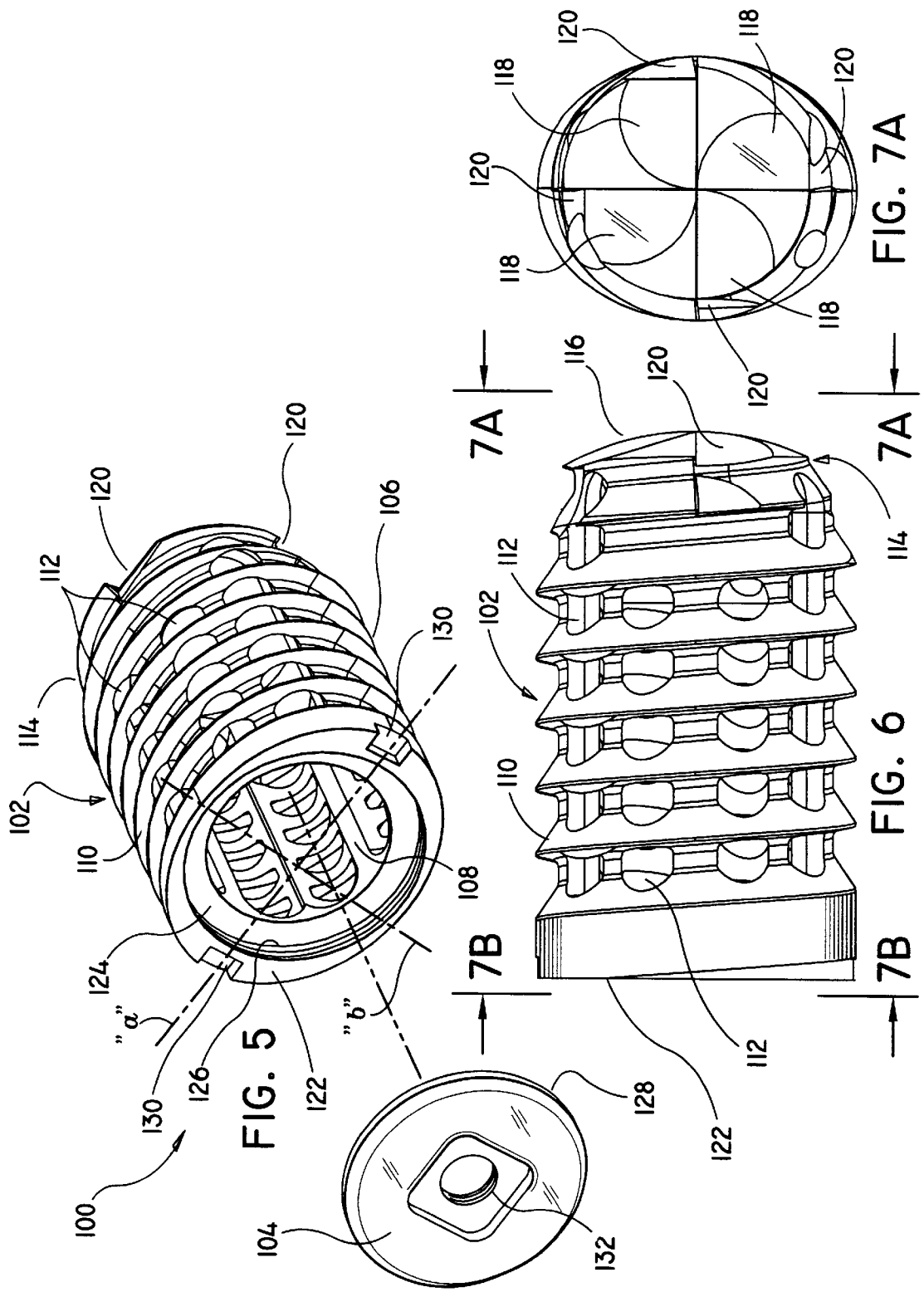

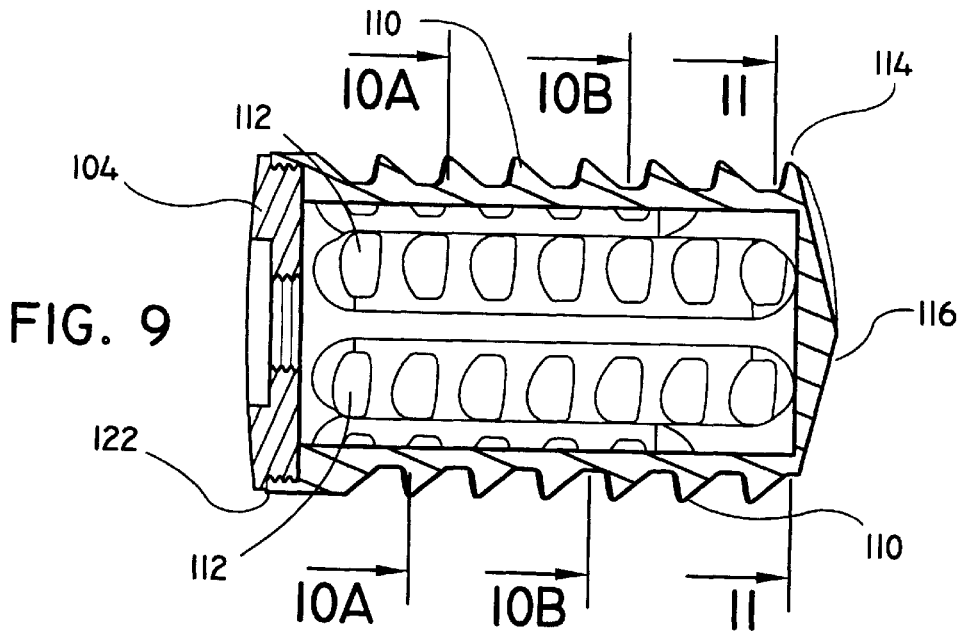
FIG. 9
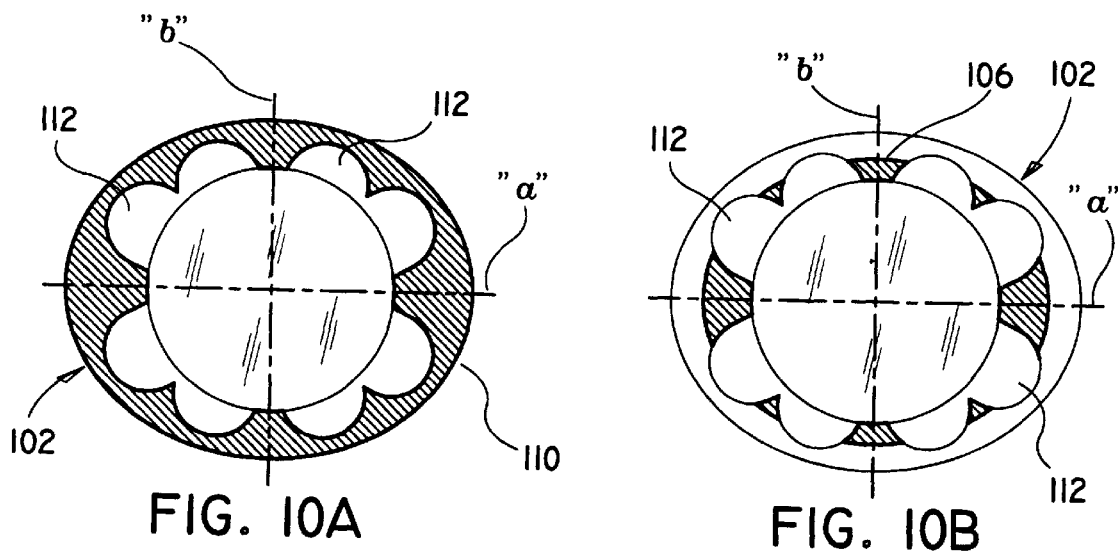
FIG. 10A
FIG. 10B
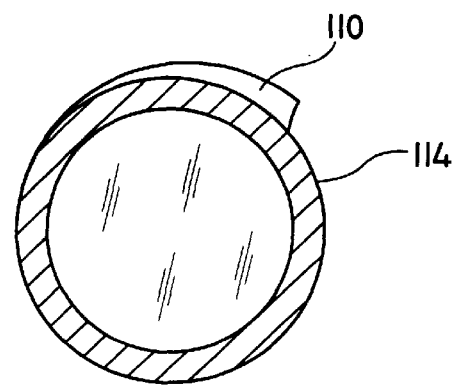
FIG. 11

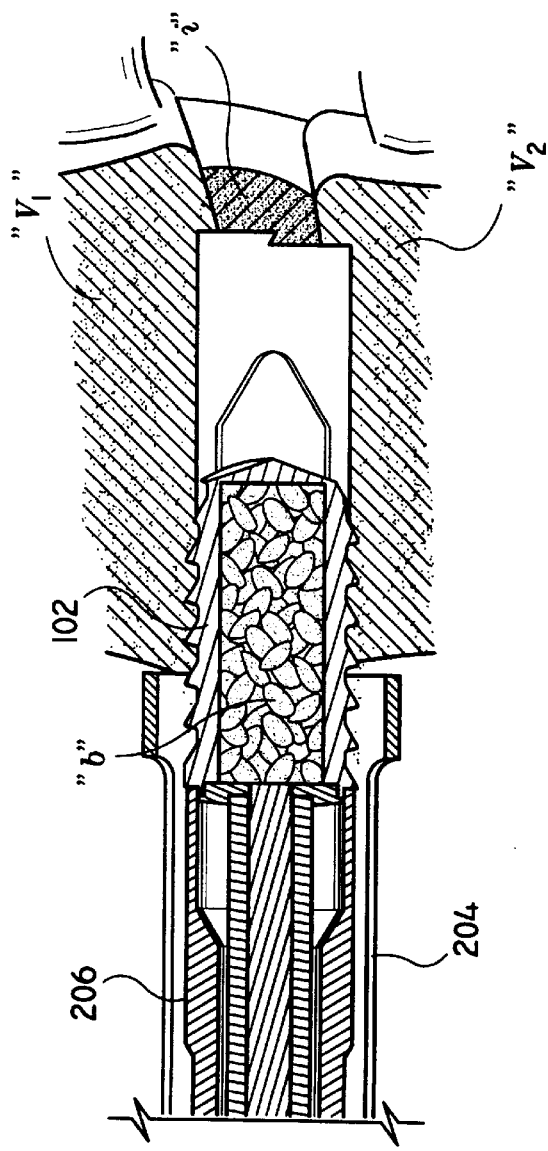
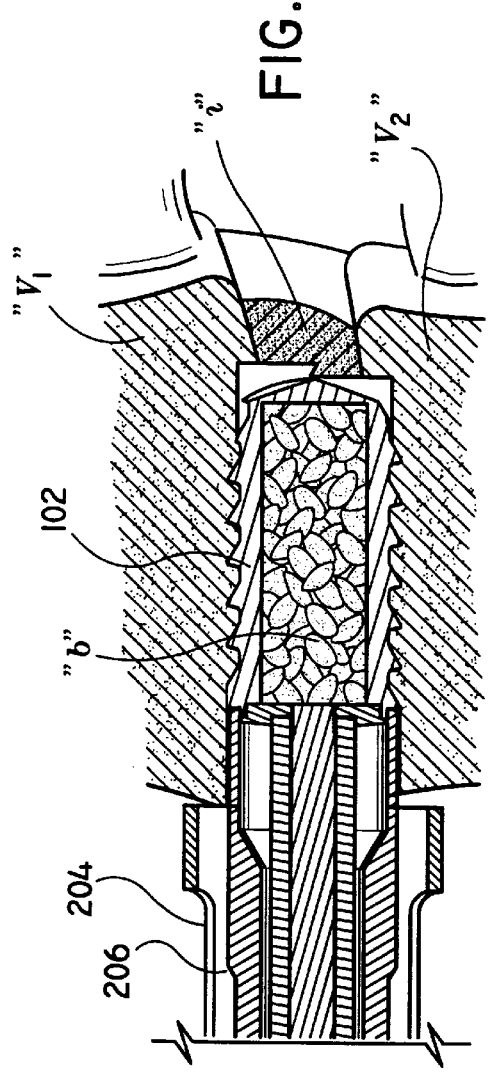

APPARATUS FOR FUSING ADJACENT BONE STRUCTURES

BACKGROUND

1. Technical Field

The present disclosure generally relates to a surgical apparatus for fusing adjacent bone structures, and, more particularly, to an apparatus and associated method for fusing adjacent vertebrae.

2. Background of the Related Art

The fusion of adjacent bone structures is commonly performed to provide for long-term replacement to compensate for degenerative or deteriorated disorders in bone. For example, an intervertebral disc, which is a ligamentous cushion disposed between adjacent vertebrae, may undergo deterioration as a result of injury, disease, tumor or other disorders. The disk shrinks or flattens leading to mechanical instability and painful disc translocations.

Conventional procedures for disc surgery include partial or total excision of the injured disc portion, e.g., discectomy, and replacement of the excised disc with biologically acceptable plugs or bone wedges. The plugs are driven between adjacent vertebrae to maintain normal intervertebral spacing and to achieve, over a period of time, bony fusion with the plug and opposed vertebrae. For example, U.S. Pat. No. 4,887,020 to Vich discloses a threaded cylindrical bone plug which is screwed into a correspondingly dimensioned cylindrical bore drilled in the intervertebral space. Other bone grafting plugs are disclosed in U.S. Pat. No. 4,950,296.

More recently, emphasis has been placed on fusing bone structures (i.e., adjoining vertebrae) with prosthetic cage implants. One fusion cage implant is disclosed in commonly assigned U.S. Pat. No. 5,026,373 to Ray et al., the contents of which are incorporated herein by reference. The Ray '373 fusion cage includes a cage having a thread formed as part of its external surface and apertures extending through its wall which communicate with an internal cavity of the cage body. The fusion cage is inserted within a tapped bore or channel formed in the intervertebral space thereby stabilizing the vertebrae and maintaining a pre-defined intervertebral space. Preferably, a pair of fusion cages are implanted within the intervertebral space. The adjacent vertebral bone structures communicate through the apertures and with bone growth inducing substances which are within the internal cavity to unite and eventually form a solid fusion of the adjacent vertebrae. FIGS. 1–2 illustrate the insertion of a pair of the Ray '373 fusion cages positioned within an intervertebral space.

SUMMARY

Although the Ray '373 fusion cage implant has proven to be effective in stabilizing the vertebrae and promoting vertebral fusion subsequent, for example, discectomy, the present disclosure is directed to further improvements in interbody fusion.

Accordingly, an apparatus for facilitating the fusion of adjacent bone structures is disclosed. The apparatus includes an implant member configured for insertion within a space defined between adjacent bone structures and having an entry end portion and a trailing end portion. The implant member includes at least a longitudinal portion having a generally elliptical cross-sectional dimension transverse to a longitudinal axis of the implant member. The elliptical configuration enhances the supporting characteristics of the implant member by increasing surface area contact of the implant member with the bone structures.

The implant member preferably includes an exterior surface portion having discontinuities to permit bone ingrowth. The external surface portion may also include a threaded portion to facilitate insertion between adjacent bone structures. A hollow interior cavity is defined within the implant member to accommodate bone growth inducing substances to facilitate the fusion process. A plurality of apertures extend through the external surface portion in communication with the interior cavity wall portion, to thereby permit bone ingrowth to facilitate fusion of the adjacent bone structure.

The entry end portion of the implant member defines a generally circular cross-sectional dimension transverse to the longitudinal axis to facilitate positioning between the adjacent bone structures. The entry end portion includes closed entry end surface.

At least one flute may be formed on the exterior surface portion to capture bone material removed during insertion of the implant within the bone structures. The one flute is disposed adjacent the entry end portion and is formed in the threaded portion. Preferably, the one flute extends to the closed entry end surface.

An apparatus for facilitating fusion of adjacent vertebrae is also disclosed. The apparatus includes an implant member configured and dimensioned for insertion within an intervertebral space defined between adjacent vertebrae. The implant member includes at least a longitudinal section having a transverse cross-sectional dimension defining a generally elliptical configuration. The implant member includes an internal cavity for accommodating bone growth inducing substances and a plurality of apertures extending through an external wall portion thereof in communication with the internal cavity. An external threaded portion is formed on the implant member for facilitating insertion within the intervertebral space.

A method for fusion of adjacent lumbar vertebrae is also disclosed.

BRIEF DESCRIPTION OF THE DRAWINGS

Preferred embodiment(s) of the present disclosure are described herein with reference to the drawings wherein:

FIG. 5 is a perspective view of the fusion implant of FIGS. 3–4 illustrating the implant body and detachable end cap;

FIG. 6 is a side plan view of the implant body;

FIG. 7A is an axial view taken along line 7A—7A of FIG. 6 illustrating the entry end portion of the implant body;

FIG. 9 is a top cross-sectional view of the implant body and mounted end cap taken along line 9—9 of FIG. 7B;

FIG. 10A is a cross-sectional view taken along line 10A—10A of FIG. 9 illustrating a section through the major diameter of the thread;

FIG. 10B is a cross-sectional view taken along line 10B—10B of FIG. 9 illustrating a section through the minor diameter of the thread;

FIG. 11 is a cross-sectional view taken along line 11—11 of FIG. 9 illustrating the circular configuration of the entry end portion of the implant body;

FIGS. 18–20 are enlarged views illustrating positioning of the fusion implant within the preformed bore;

DETAILED DESCRIPTION OF PREFERRED EMBODIMENTS

The preferred embodiment of the apparatus and method disclosed herein are discussed in terms of orthopedic spinal fusion procedures and instrumentation. It is envisioned, however, that the disclosure is applicable to a wide variety of procedures including, but, not limited to ligament repair, joint repair or replacement, non-union fractures, facial reconstruction and spinal stabilization. In addition, it is believed that the present method and instrumentation finds application in both open and minimally invasive procedures including endoscopic and arthroscopic procedures wherein access to the surgical site is achieved through a cannula or small incision.

The following discussion includes a description of the fusion implant utilized in performing a spinal fusion followed by a description of the preferred method for spinal fusion in accordance with the present disclosure.

In the discussion which follows, the term "proximal", as is traditional, will refer to the portion of the structure which is closer to the operator, while the term "distal" will refer to the portion which is further from the operator.

Fusion Implant

Figure 3:
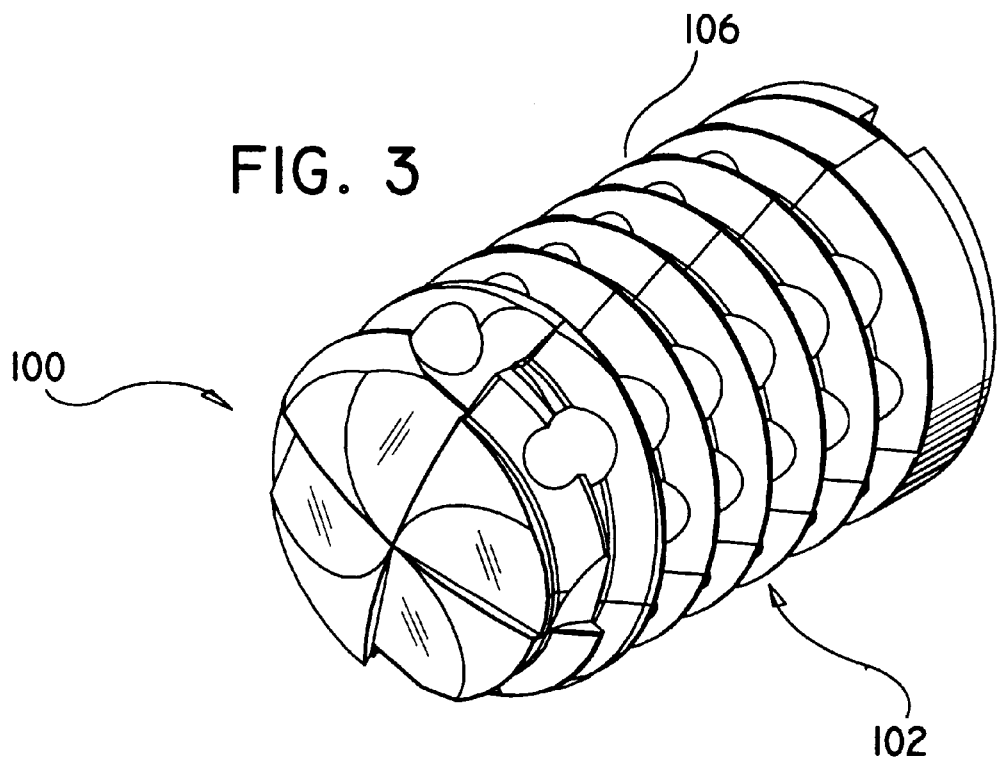
FIGS. 3–4 are front and rear perspective views of the fusion implant in accordance with the principles of the present disclosure.
Figure 4:
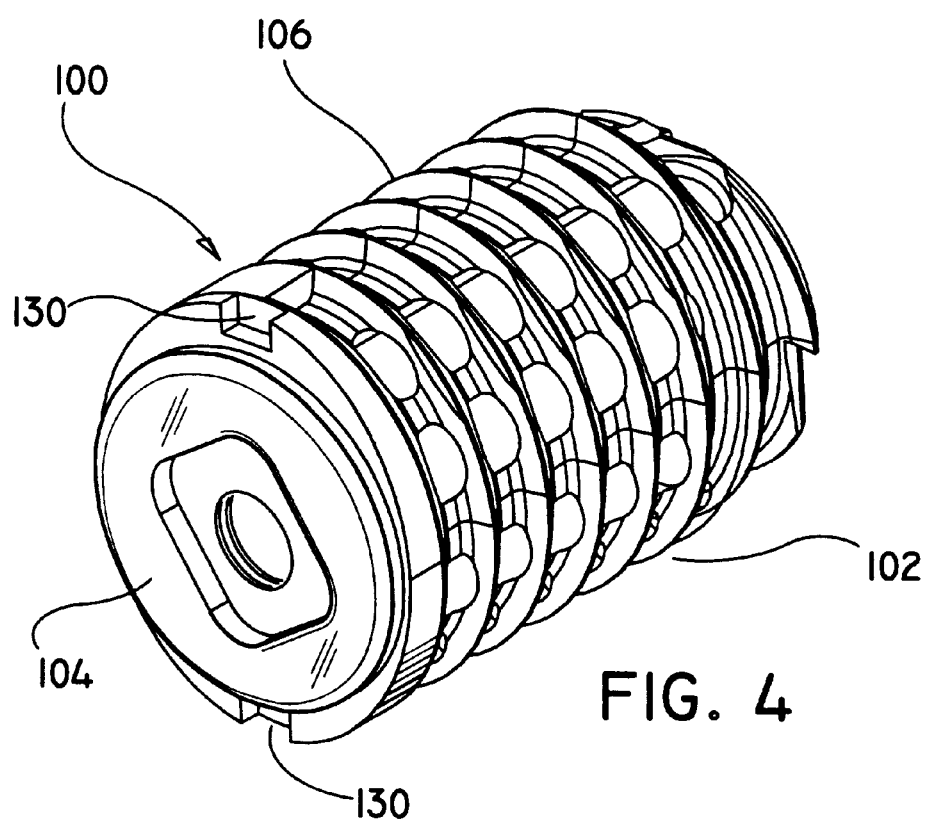
Figure 8:
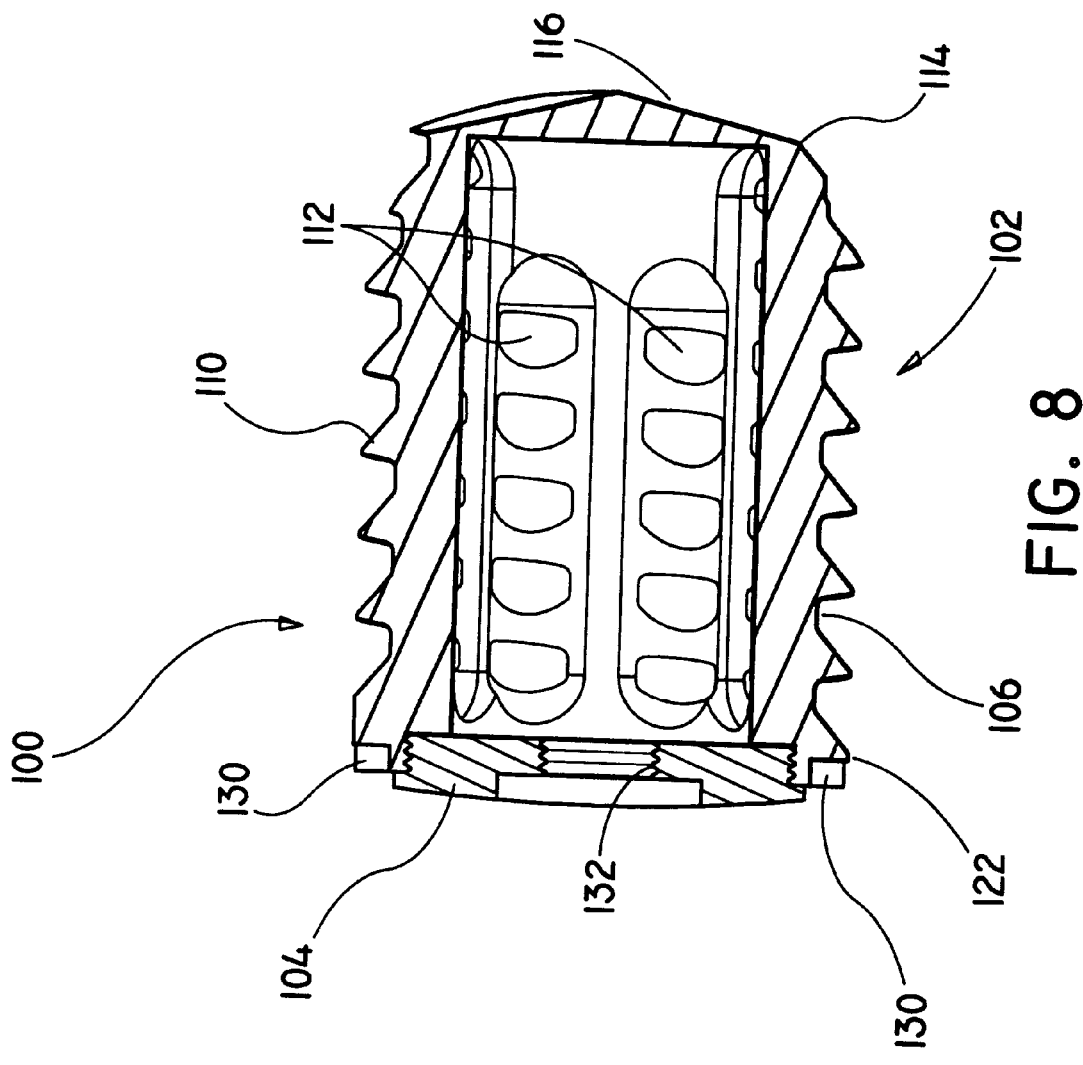
FIG. 8 is a side cross-sectional view of the implant body and mounted end cap taken along line 8—8 of FIG. 7B.

Referring now to the drawings in which like reference numerals identify similar or identical elements throughout the several views, FIGS. 3–5 illustrate in perspective the fusion implant of the present disclosure. Fusion implant 100 is contemplated to be a self-tapping implant, i.e., the implant is intended to be inserted within a preformed bore in adjacent bone structures, e.g., adjacent vertebrae, without necessitating tapping of an internal thread within the bone structures prior to insertion and is preferably configured for lumbar vertebrae. Fusion implant 100 includes elongated implant body 102 and end cap 104 which is mountable to the implant body 102. Implant body 102 is preferably fabricated from a suitable biocompatible rigid material such as titanium and/or alloys of titanium, stainless steel, ceramic materials or rigid polymeric materials. Implant body 102 is preferably sufficient in strength to at least partially replace the supporting function of an intervertebral disc, i.e., to maintain adjacent vertebrae in desired spaced relation, during healing and fusion, and is strategically dimensioned to span the intervertebral space such that only one implant (as opposed to two as is conventional) is required for insertion. The implant 100 is preferably provided in various lengths such as about 24 mm, 26 mm and 28 mm for example.

As best depicted in FIGS. 5–7B, implant body 102 is generally elliptical in configuration defining a major axis "a" greater than a minor axis "b" (FIG. 5). This configuration provides a greater surface area of the implant so as to facilitate contacting engagement and support of the implant with the adjacent vertebrae. In particular, as discussed in greater detail hereinbelow, in the inserted position of the fusion implant 100, the major axis "a" is in general parallel relation with the vertebral end faces of the adjacent vertebrae, thus, positioning the major arc or outer surface of implant body 102 in contact with the vertebral end faces. The oval or elliptical configuration and dimensions enable one implant to be utilized instead of two implants of the prior art. The elliptical configuration of implant body 102 also minimizes any tendency of the inserted implant 100 from backing out of the preformed bore. Implant body 102 includes an outer wall 106 which enclose an inner cavity 108 defined within the interior of the implant body 102. Inner cavity 108 accommodates bone growth inducing substances which facilitate the fusion process.

In a preferred embodiment, the diameter of the implant 102 along its major axis preferably ranges from about 16 mm to about 20 mm, and preferably is about 19 mm. The diameter along the minor axis preferably ranges from about 14 mm to about 17 mm, and preferably is about 16 mm. Other dimensions are also contemplated.

With reference to FIGS. 8–10B, in conjunction with FIG. 5, outer wall 106 has an external threaded configuration formed as part of its exterior surface. External threaded configuration including a continuous helical thread 110 which assists in advancing implant body 102 into a preformed channel provided in the adjacent vertebrae. Thread 110 as shown preferably has an angled face on the posterior side and a sharp end toward the anterior side to prevent expulsion to the anterior side. Thread 110 is preferably a self-tapping cutting thread, i.e., the threads are capable of deburring bone material during advancement into the performed channel. Alternatively, a thread can be tapped in the bone prior to insertion of the implant.

A plurality of apertures 112 extend through outer wall 106 of implant body 102. Apertures 112 are preferably formed by broaching grooves in the internal surface of the internal cavity 108. The effect of such broaching is to remove material from the valleys between the threads 110, thus defining the apertures 112. The advantages of such an arrangement are disclosed in U.S. Pat. No. 4,961,740, the contents of which are incorporated herein by reference, and include immediate bone to bone contact between the vertebral bodies or bone structures and the bone inducing substances packed within the internal cavity 108 of the implant body 102. Apertures 112 are preferably substantially the same in dimension although it is envisioned that the dimensions of the apertures may vary to provide for more or less bone to bone contact as desired.

As best depicted in FIGS. 10A–10B, apertures 112 are clustered about a transverse axis or minor axis "b", both at the upper and lower end of the axis. Consequently, apertures 112 come into contact with the upper and lower vertebral bone structures to encourage bone growth through implant body 102 from the vertebral bone structures. The lateral sections of implant body 102 formed along the major axis "a" do not have apertures in order to prevent growth of disk material which might interfere with the bone fusing process.

With reference now to FIGS. 6–7A and 11, the entry or leading end potion (distal) 114 of implant body 102 is preferably rounded, i.e., generally circular in cross-section as best depicted in FIG. 11 and defines a closed rounded entry end surface 116. This facilitates insertion. End surface 116 includes a plurality of flutes or relief grooves 118 formed in its surface. (four are shown). Flutes 118 assist in insertion of fusion implant 100 within the intervertebral space by capturing bone material deburred during the self-tapping process. In a preferred embodiment, flutes 118 meet at a central point of the longitudinal axis on the entry end of surface 116 and extend proximally to at least the first turn of the thread on implant body 102. The flute portions formed on thread 110 are defined by the sections 120 which are removed from the thread. (See also FIG. 5.) This arrangement permits adequate relief for purposes of self tapping of implant 100 in the intervertebral space. It is also envisioned that the flutes may run deeper and extend from the leading end 114 completely to the end cap 104, or, to a position intermediate the end cap 104 and the leading end 114.

Figure 7B:
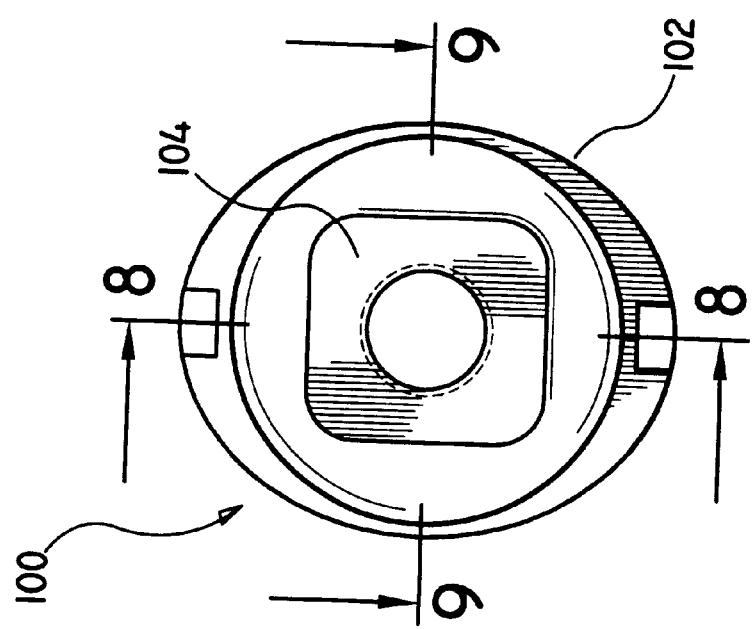
FIG. 7B is an axial view taken along lines 7B—7B of FIG. 6 illustrating the trailing end portion of the fusion implant.

With reference now to FIG. 5 and FIG. 7B, the trailing end portion 122 of implant body 102 has a generally annular recess 124 which receives end cap 104. An internal thread 126 is disposed adjacent annular recess 124 and cooperates with external thread 128 on the periphery of end cap 104 to mount the end cap to implant body 102. Trailing end portion 122 also includes a pair of diametrically opposed notches 130. Notches 130 are dimensioned to be engaged by corresponding structure of an insertion apparatus utilized in inserting the implant within the vertebral column. End cap 104 includes a central threaded aperture 132 which threadably engages corresponding structure of the insertion apparatus to assist in the mounting of the cap 104 on implant body 102.

Instrumentation Kit

Figure 12:
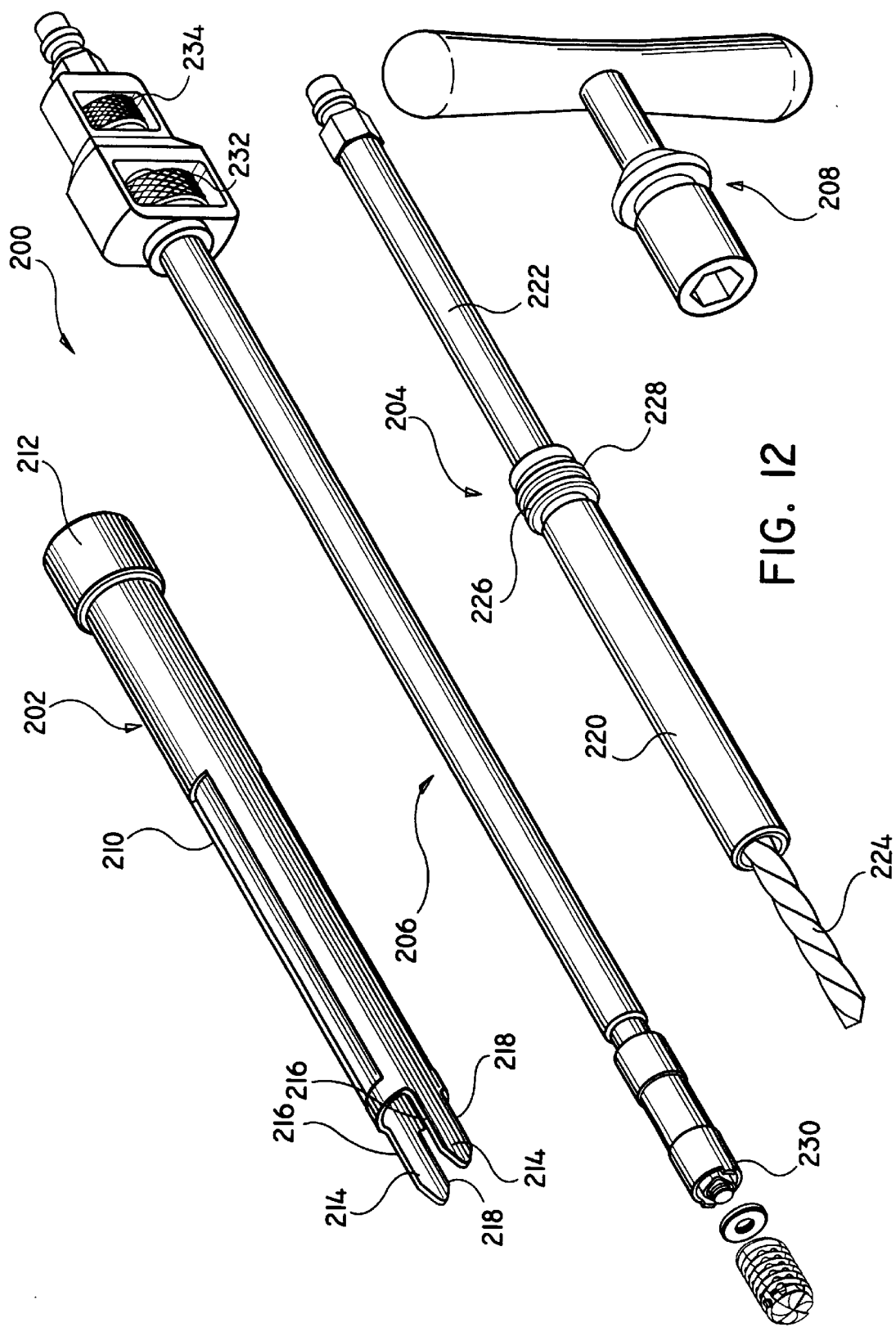
FIG. 12 is a perspective view of an instrumentation kit utilized for inserting the fusion implant within the intervertebral space, including a surgical retractor, a surgical drill, an implant insertion instrument and a T-shaped handle.

Referring now to FIG. 12, there is illustrated an instrumentation kit for inserting spinal implant 100 within the intervertebral space. The instrumentation kit 200 includes surgical retractor 202, drill instrument 204 and insertion instrument 206. A T-shaped handle 208 is also provided in kit 200, and is utilized to actuate drill instrument 204 and insertion instrument 206.

Surgical retractor 202 is disclosed in commonly assigned U.S. patent application Ser. No. 08/615,379, filed Mar. 14, 1996, the contents of which are incorporated herein by reference. Retractor 202 is configured for distracting adjacent vertebral bodies to facilitate the insertion and application of an implant, for providing a cannula for insertion of the instruments, and for ensuring proper alignment of the instrumentation and accurate insertion of the implant.

Retractor 202 includes sleeve 210 with an enlarged head 212 at the proximal end of the sleeve 210. Sleeve 210 includes first and second diametrically opposed retractor arms 214 having first and second parallel vertebrae supporting surfaces 216, 218.

Drill instrument 204 is also disclosed in the '379 application. Drill instrument 204 includes drill shaft 220, extension shaft 222 and drill bit 224 mounted at the distal end of the drill shaft. T-handle 208 is mountable to a proximal mounting section of the drill instrument 204. Extension shaft 222 has first and second collars 226, 228 which cooperate to control the depth of penetration of drill shaft 220 into the adjacent vertebrae.

Insertion instrument 206 is disclosed in commonly assigned U.S. patent application Ser. No. 08/616,120, filed Mar. 14, 1996, the contents of which are also incorporated herein by reference. Insertion instrument 206 includes implant engaging structure 230 at its distal end which is correspondingly configured to mount and release implant 100 as will be discussed herein below. A pair of control wheels 232, 234 serve to control actuation of insertion instrument 206 thereby controlling mounting and releasing of the implant within the intervertebral space.

Insertion of Fusion Implant With Instrumentation Kit

The insertion of the fusion implant 100 with the instrumentation kit 200 into an intervertebral space defined between adjacent lumbar vertebrae will now be described. The subsequent description will be particularly discussed in conjunction with an open antero-lateral approach for spinal fusion implant insertion. However, it is to be appreciated that other approaches, e.g., posterior, direct anterior, etc . . . could be utilized. Laparoscopic approaches are also envisioned.

Figure 13:
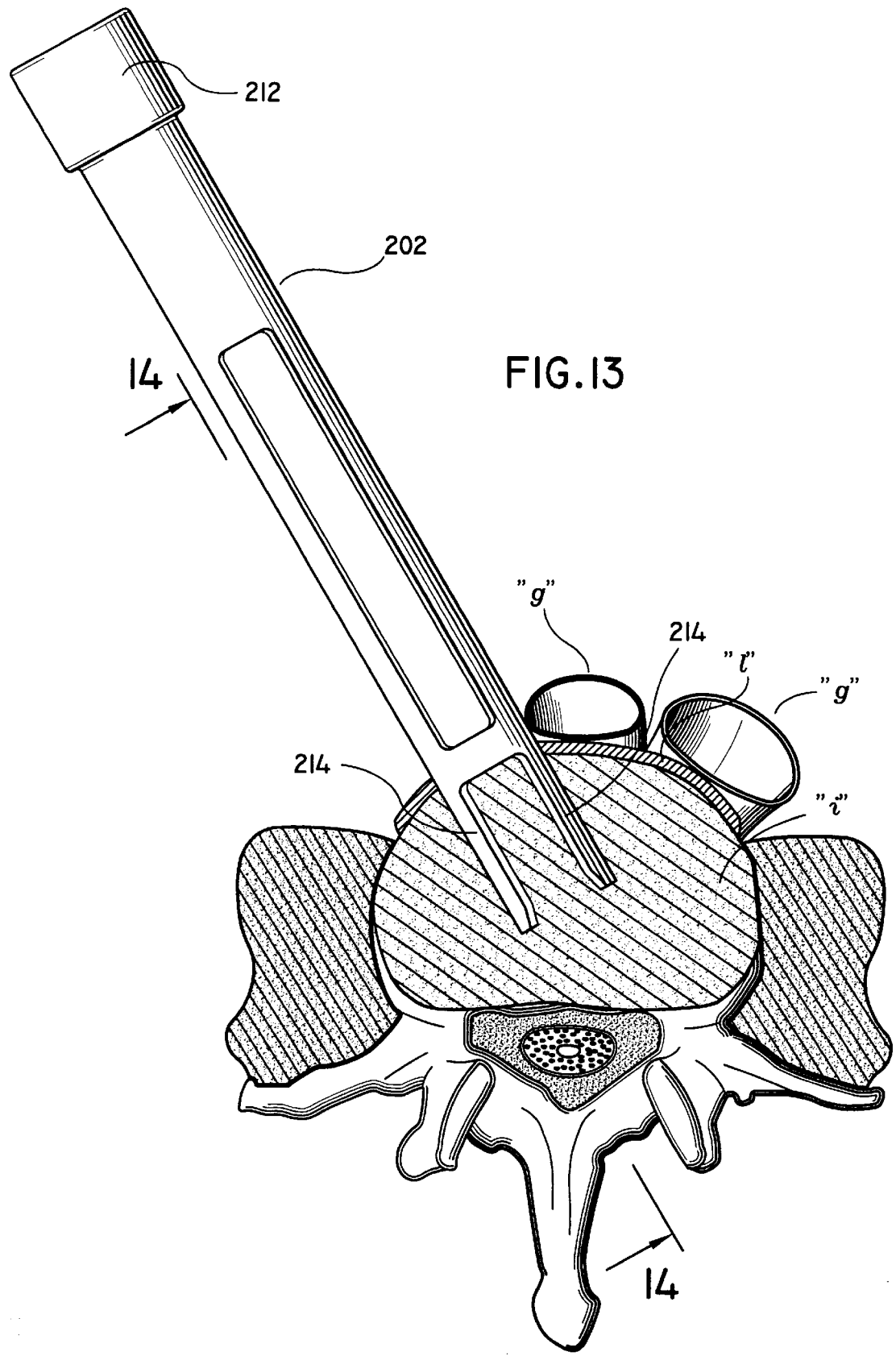
FIG. 13 is a view illustrating the lateral insertion of the surgical retractor within the intervertebral space.

With respect now to FIG. 13, the intervertebral space "i" is accessed utilizing appropriate retractors to expose the anterior vertebral surface. Thereafter, retractor 202 is inserted within the intervertebral space "i" from an antero-lateral or oblique approach with relation to the vertebral columns 216, 218 as depicted in FIG. 13. Such approach provides advantages with regard to avoiding interference by the great vessels "g" (FIG. 13) and limiting penetration of the anterior longitudinal ligament "l". The retractor may be inserted by placing an impactor cap at the proximal end and impacting the retractor into the intervetebral space.

Figure 14:
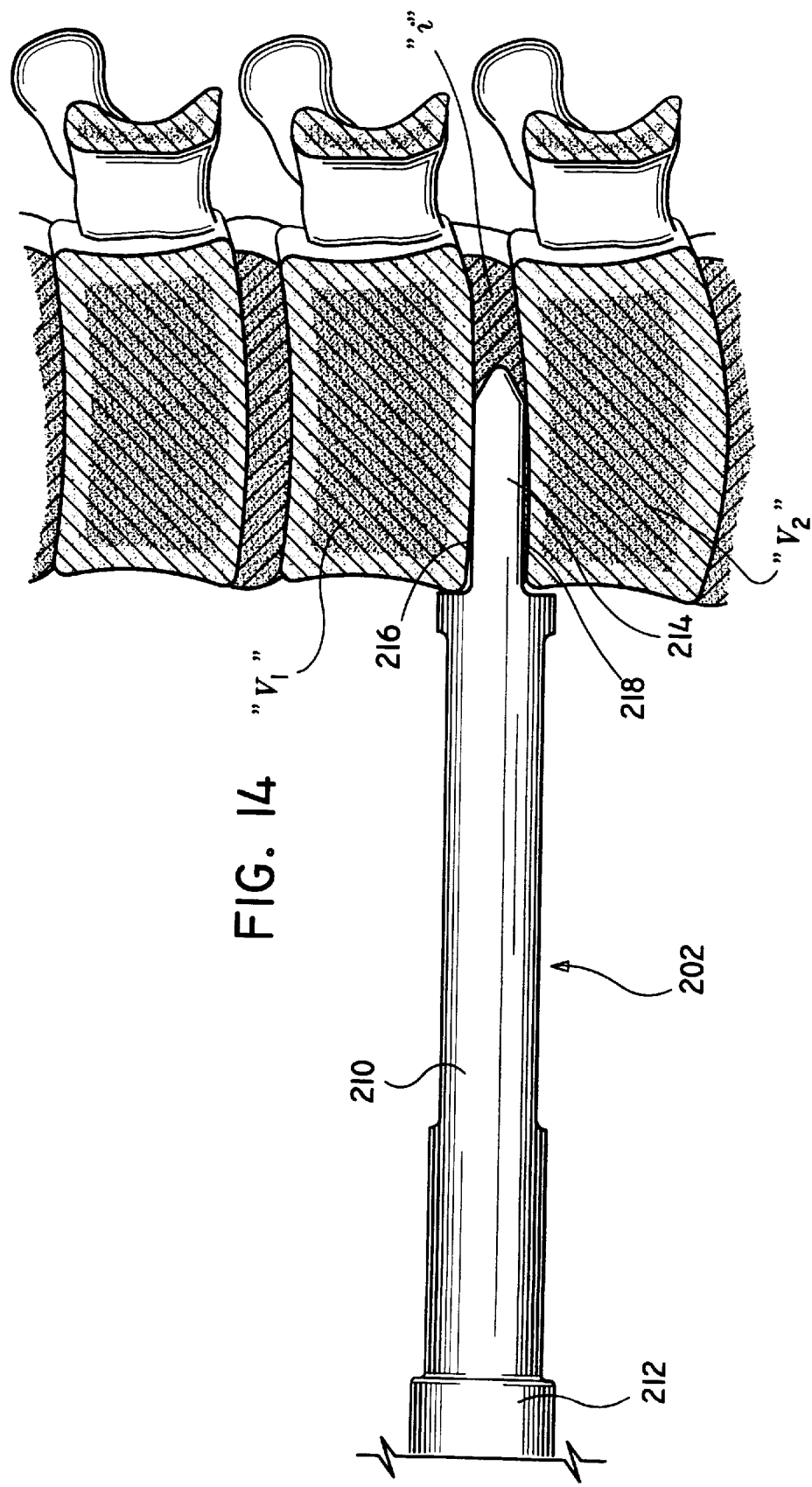
FIG. 14 is a view taken along line 14—14 of FIG. 13 further illustrating positioning of the retractor within the intervertebral space and engagement of the retractor with the vertebral end faces of the adjacent vertebrae.

FIG. 14 depicts retractor 202 positioned within the intervertebral space "i" with the retractor arms 214 arranged such that the first and second supporting surfaces 216, 218 of each retractor arm 214 respectively engage the opposed vertebral bodies "$V_1$, $V_2$". Upon insertion of retractor arms 214, the vertebral bodies "$V_1$, $V_2$" are distracted whereby the retractor arms become firmly lodged within the intervertebral space "i".

Figure 15:
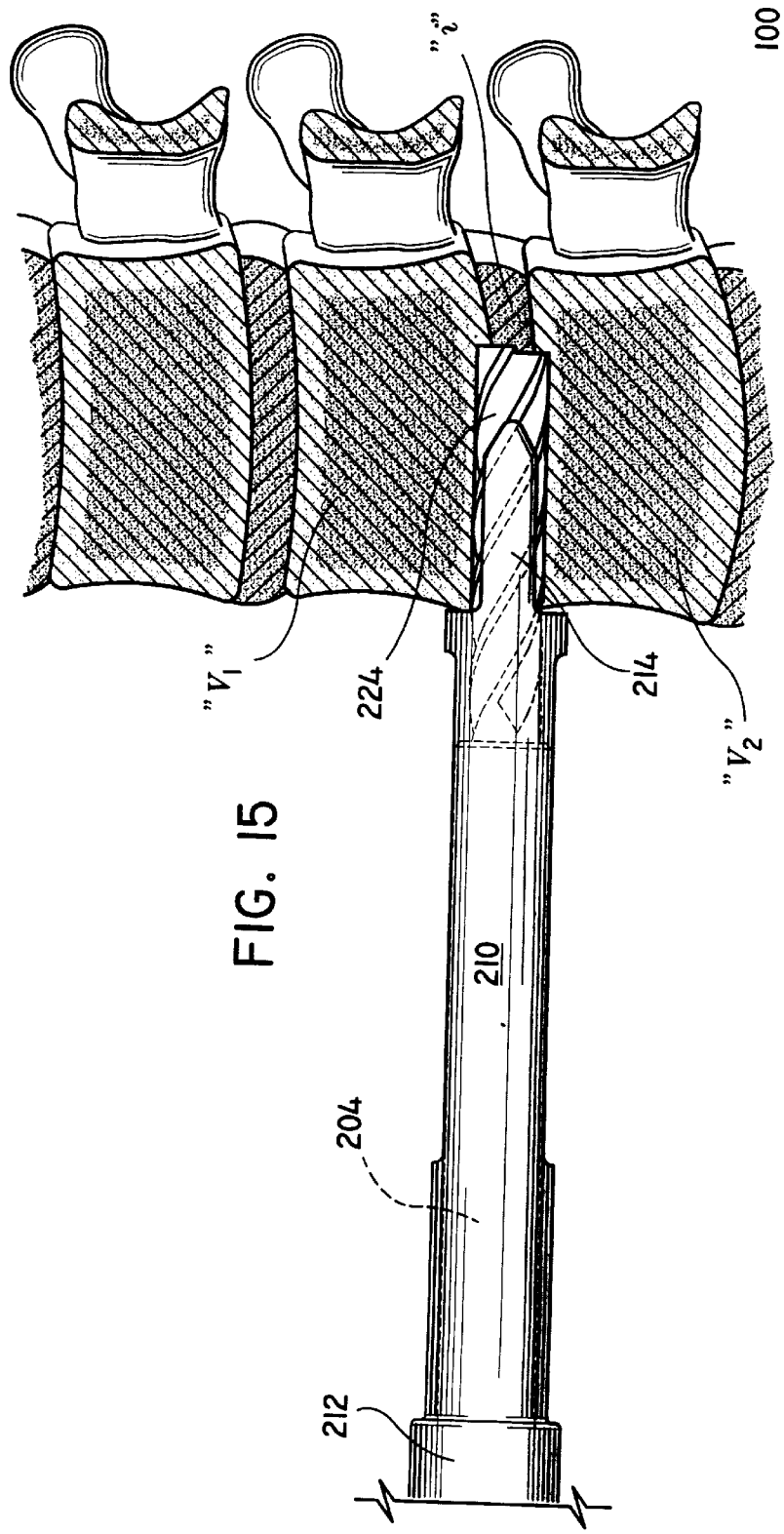
FIG. 15 is a view similar to the view of FIG. 14 illustrating insertion of a drilling instrument into the retractor to drill a bore within the adjacent vertebrae.

Referring now to FIG. 15, the drilling instrument 204 is now utilized to prepare the disc space and vertebral end plates for insertion of the fusion implant. The cutting depth of drilling instrument 204 is adjusted as desired (i.e., to correspond to the length of the fusion implant) by adjusting collars 226, 228. With the T-handle 208 mounted to drilling instrument 204, the instrument is introduced into retractor 202 and advanced to contact the anterior surface of the vertebral bodies "$V_1$ $V_2$". Drilling instrument 204 is advanced into the intervertebral space "i" by rotating T-handle 208 to shear the soft tissue and cut the bone of the adjacent vertebrae "$V_1$ $V_2$" thereby forming a bore which extends into the adjacent vertebrae "$V_1$, $V_2$".

Figure 16:
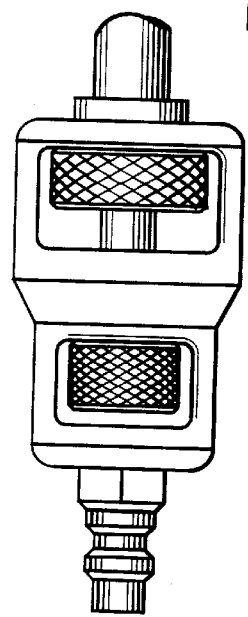
FIG. 16 is a side plan view illustrating the insertion instrument with the fusion implant mounted to the insertion instrument.
Figure 16A:
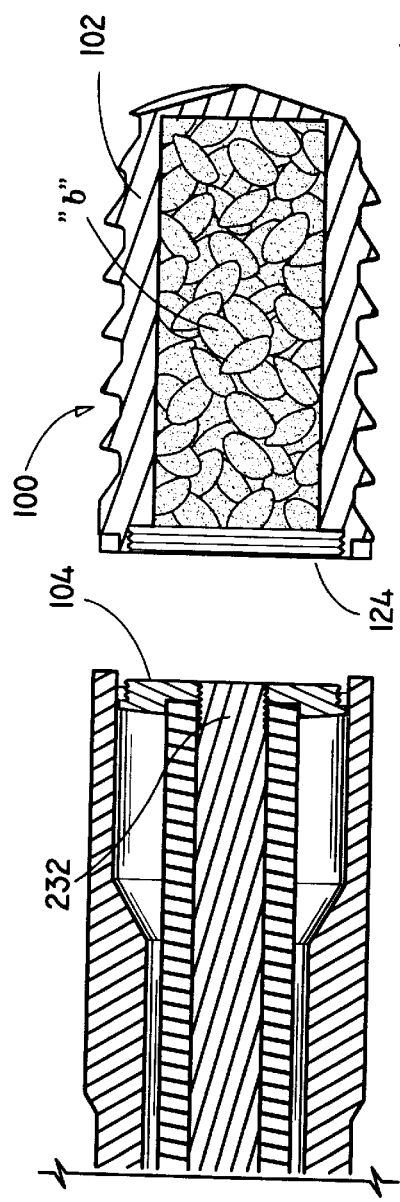
FIG. 16A is a cross-sectional view of the distal end of the insertion instrument and the fusion implant illustrating mounting of the end cap to the implant body.

Subsequent to the drilling process, fusion implant 100 is packed with bone growth inducing substances "b" as in conventional in the art and end cap is threaded into recess 124 of implant body 102 either by hand, with a socket wrench-type instrument or with insertion instrument 206 as depicted in FIG. 16A. In particular, as shown in FIG. 16A, end cap 104 may be threaded onto mounting screw 232 of insertion instrument 206 and then threaded into recess 124 of implant body 102 via rotation of wheel 232. The fusion implant 100 is then mounted on insertion instrument 206 by positioning distal tabs 234 of insertion instrument 206 within correspondingly dimensional recesses 128 of end cap 104 (FIG. 5). FIG. 16 illustrates fusion implant 100 mounted to insertion instrument 206. Further details of the mounting of implant 100 to insertion instrument 206 may be ascertained by reference to the '120 application.

Figure 17:
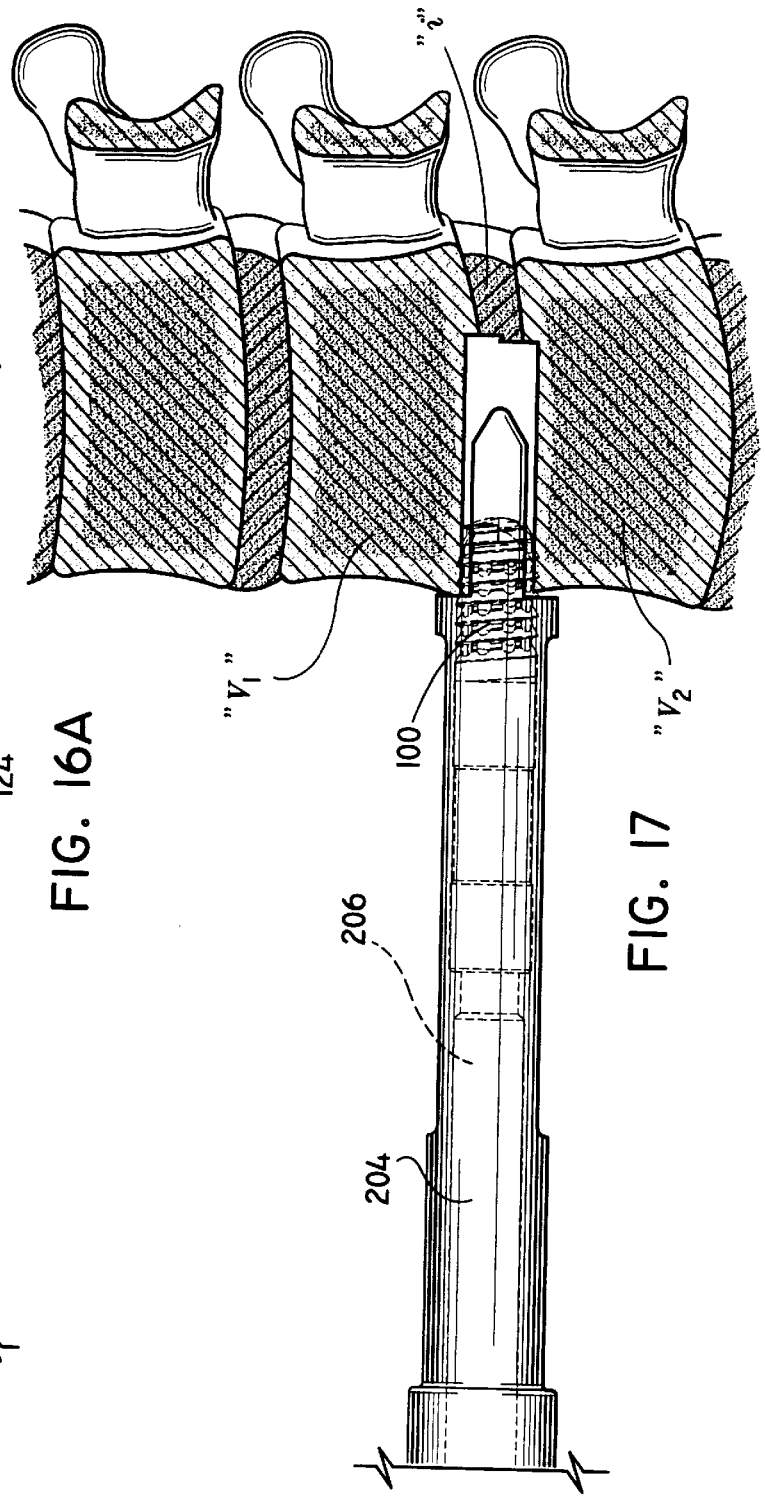
FIG. 17 is a view similar to the view of FIG. 15 illustrating insertion of the insertion instrument and mounted implant through the retractor.

Referring now to FIG. 17, insertion instrument 206 and mounted implant 100 is introduced within retractor 204 and advanced to a position adjacent the vertebral bodies "$V_1$, $V_2$". Thereafter, insertion instrument 206 is rotated via T-shaped handle 202 which is mounted to the instrument 206 to thereby cause corresponding rotation of fusion implant 100. As fusion implant 100 rotates, the thread 110 of the implant body 102 bites into the vertebral bodies "$V_1$, $V_2$". Continued rotation of insertion tool 206 causes implant to move through the position shown in FIG. 18 to the position shown in FIG. 19 to be self-tapped within the preformed bore. Implant 100 is released from its mounting to insertion tool 206 and the instrument 206 and retractor 204 are removed from the disc area.

Figure 2:
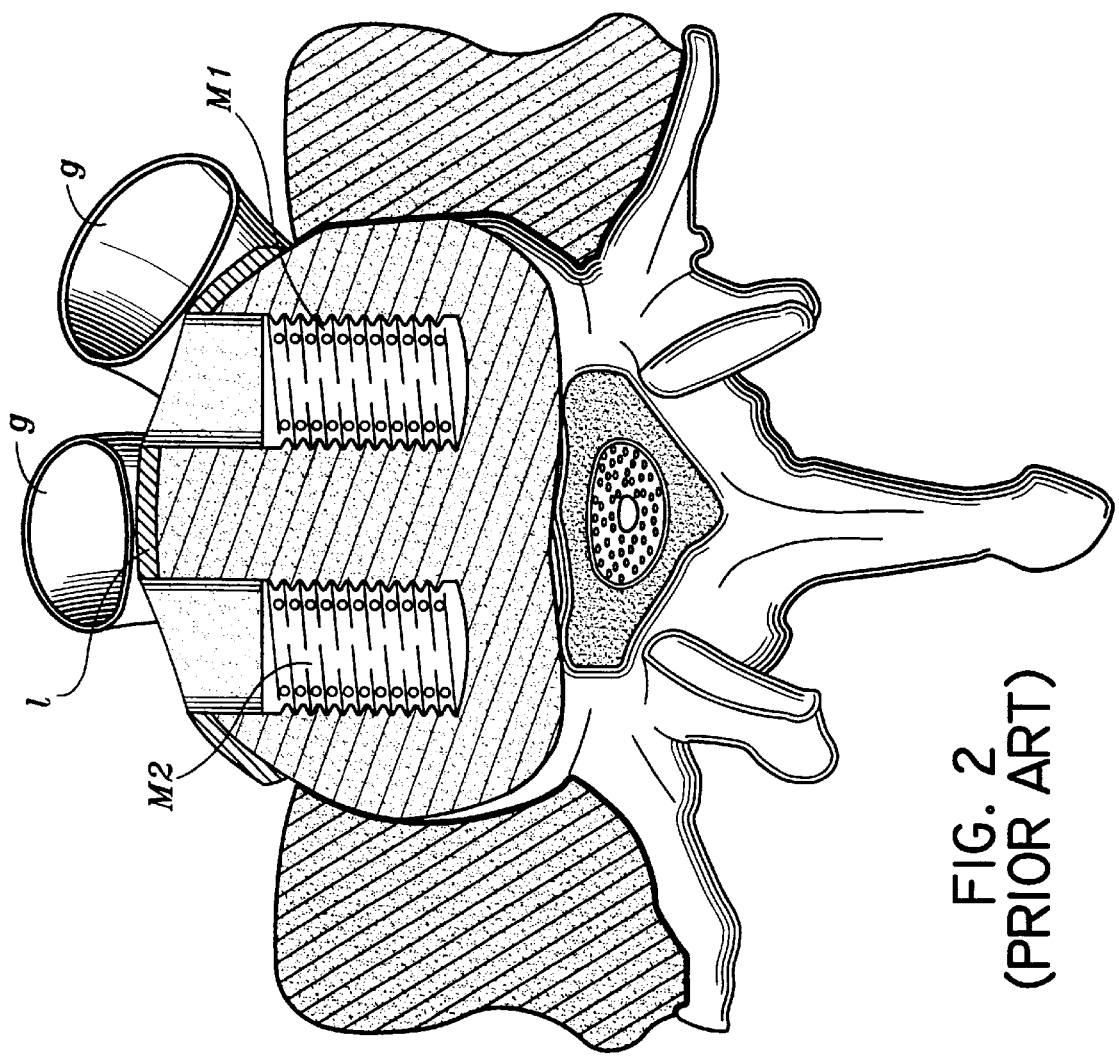
FIG. 2 is a view taken along line 2—2 of FIG. 1 illustrating a pair of prior art fusion implants positioned within the intervertebral space for fusion of adjacent vertebrae.
Figure 1:
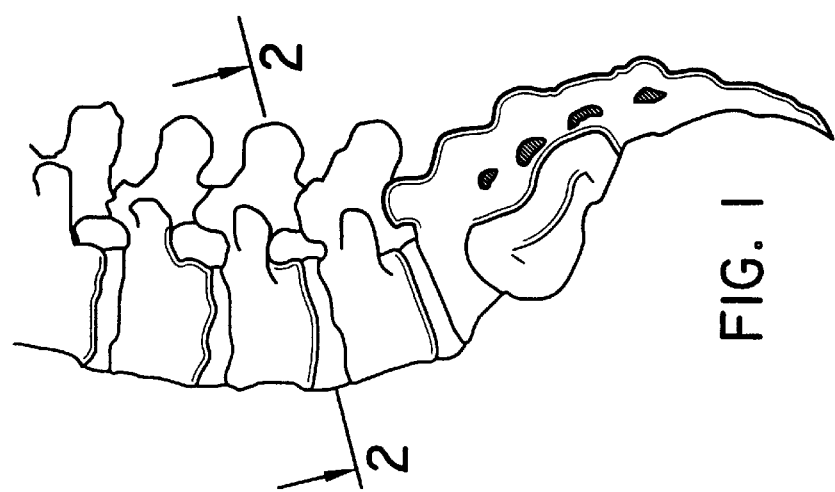
FIG. 1 is a view illustrating a portion of the vertebral column of a patient.
Figure 20:
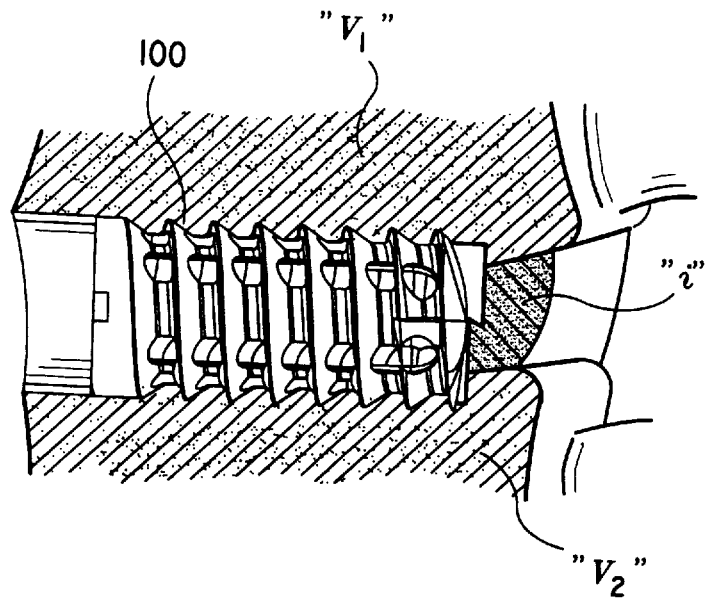
Figure 21:
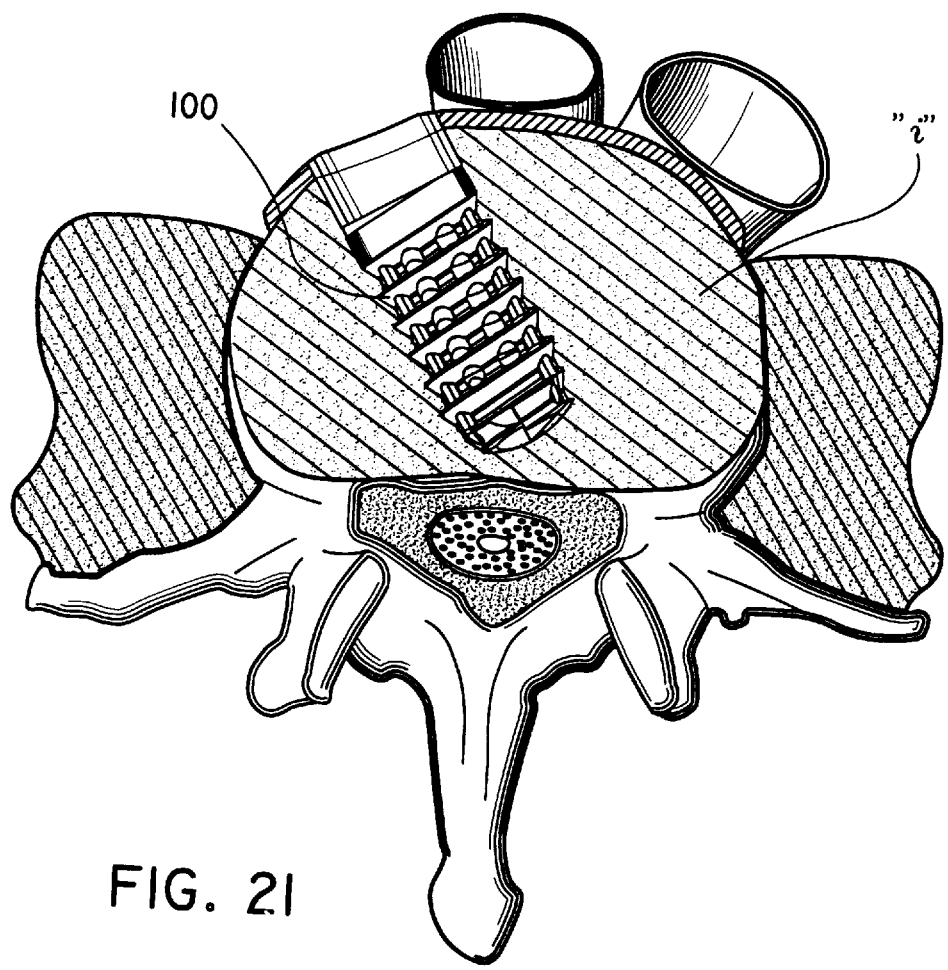
FIG. 21 is a view illustrating the fusion implant mounted within the intervertebral space.
Figure 22:
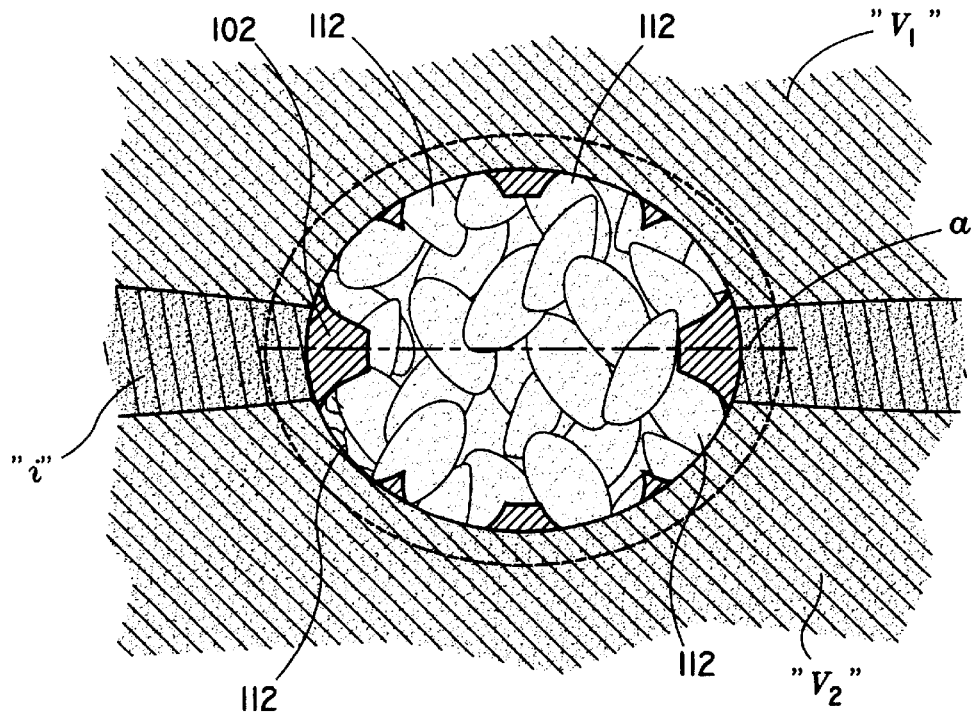
FIG. 22 is a sectional view further illustrating the fusion implant mounted within the intervertebral space.

FIGS. 20–22 depict fusion implant 100 inserted within the intervertebral space "i". As shown, fusion implant 100 forms a strut across the intervertebral space "i" to maintain the adjacent vertebrae "$V_1$, $V_2$" in appropriate spaced relation during the fusion process. The implant is thus preferably inserted at an angle of between about 15 degrees and about 45 degrees, and more preferably at about 30 degrees to the longitudinal axis of the spine and to the right of the great vessels as view anteriorly. As also shown, in the inserted position of implant 100, the major axis "a" is in general parallel relation to the vertebral end plates thus presenting the greater arc or surface area of implant body 102 to contact and support the adjacent vertebrae. Over a period of time, the adjacent vertebral tissue communicates through apertures 112 with the bone growth inducing substances "b" within the interior cavity 108 of implant to form a solid fusion. Thus only one implant is required as opposed to two implants of the prior art as shown in FIG. 2. Implantation of the implants M1, M2 of FIG. 2 require greater manipulation due to the presence of the great vessels "g" and require increased penetration of the anterior longitudinal ligament "l".

Figure 23:
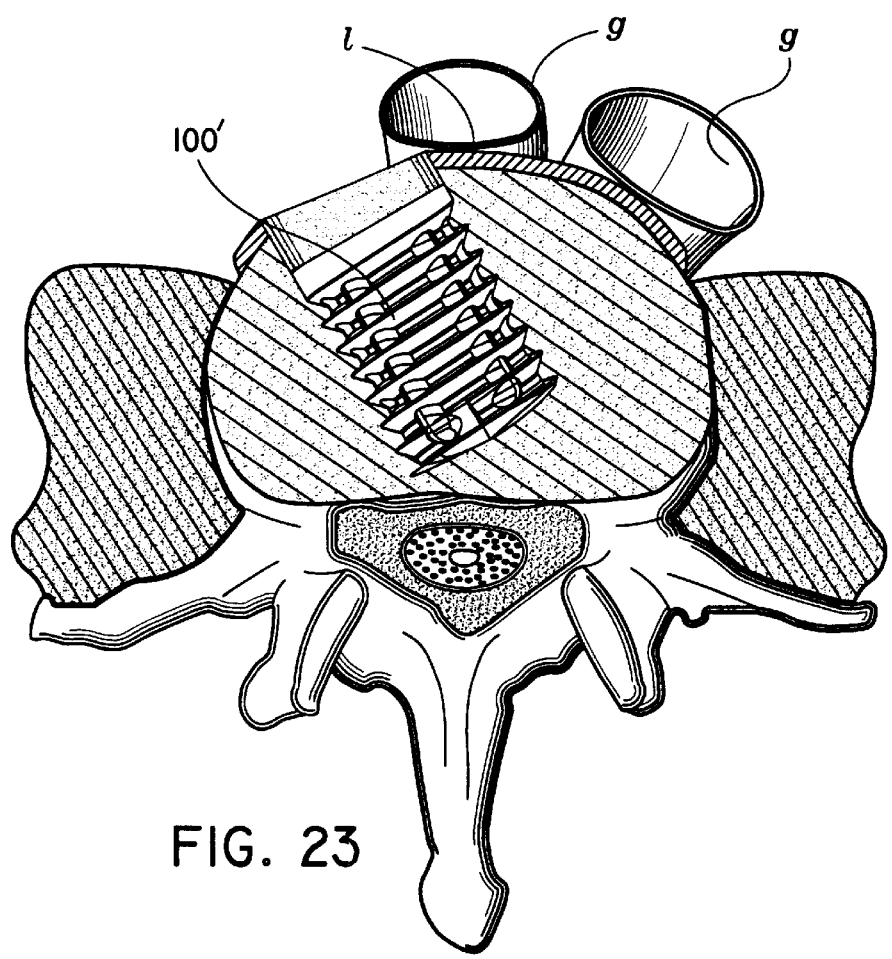
FIG. 23 is a view illustrating a different sized fusion implant mounted within the vertebral space.

FIG. 23 by way of example illustrates a different sized fusion implant 100' positioned within the intervertebral space. This cage fills a larger portion of the disc space.

While the above description contains many specifics, these specifics should not be construed as limitations on the scope of the disclosure, but merely as exemplifications of preferred embodiments thereof. For example, the fusion implant 100, 100' could also be used for thoracic and cervical vertebrae. Those skilled in the art will envision many other possible variations that are within the scope and spirit of the disclosure as defined by the claims appended hereto.

What is claimed is:

1. An apparatus for facilitating the fusion of adjacent bone structures comprising an implant member configured for insertion within a space defined between adjacent bone structures, the implant member including an entry end portion and a trailing end portion and defining a longitudinal axis, the implant member having a generally curved elliptical cross-sectional dimension transverse to the longitudinal axis along at least a portion of the length thereof, the entry end portion having a closed entry end surface.

2. An apparatus for facilitating the fusion of adjacent bone structures comprising an implant member configured for insertion within a space defined between adjacent bone structures, the implant member including an entry end portion and a trailing end portion and defining a longitudinal axis, the implant member having a generally curved elliptical cross-sectional dimension transverse to the longitudinal axis along at least a portion of the length thereof, the implant member further including an external surface portion having a threaded portion to facilitate insertion within the space defined between adjacent bone structures.

3. The apparatus according to claim 2 wherein the implant member includes a hollow interior cavity dimensioned to accommodate bone growth inducing substances.

4. The apparatus according to claim 3 wherein the implant member includes a plurality of apertures extending through an external surface portion in communication with the interior cavity, to thereby permit bone ingrowth to facilitate fusion of the adjacent bone structure.

5. The apparatus according to claim 2 wherein the entry end portion of the implant member defines a generally circular cross-sectional dimension transverse to the longitudinal axis to facilitate positioning between the adjacent bone structures.

6. The apparatus according to claim 3 wherein the implant member includes an exterior surface portion having at least one flute formed therein.

7. The apparatus according to claim 6 wherein the one flute is disposed adjacent the entry end portion and is formed in the threaded portion.

8. The apparatus according to claim 7 wherein the entry end portion includes a closed entry end surface.

9. The apparatus according to claim 8 wherein the one flute extends to the closed entry end surface.

10. An apparatus for facilitating the fusion of adjacent bone structures comprising an implant member configured for insertion within a space defined between adjacent bone structures, the implant member including an entry end portion and a trailing end portion and defining a longitudinal axis, the implant member having a generally curved elliptical cross-sectional dimension transverse to the longitudinal axis alone at least a portion of the length thereof, the implant member defining a hollow interior cavity dimensioned to accommodate bone growth inducing substances and a plurality of apertures extending through an external surface portion in communication with the interior cavity, to thereby permit bone ingrowth to facilitate fusion of the adjacent bone structure, and an end cap mountable to the trailing end portion of the implant member to enclose the interior cavity.

11. The apparatus according to claim 1 wherein the implant member is configured for insertion within the intervertebral space defined between adjacent vertebrae.

12. An apparatus for facilitating fusion of adjacent vertebrae of the spine, the adjacent vertebrae having an intervertebral disc space therebetween defining a disc height, the apparatus comprising an elongated implant member configured and dimensioned for insertion within the intervertebral space defined between adjacent vertebrae and defining a longitudinal axis, the implant member including a longitudinal section having a transverse cross-sectional dimension defining a generally curved elliptical configuration with a major axis and a minor axis to define a curved external wall portion of the longitudinal section, the implant member including an internal cavity for accommodating bone growth inducing substances and having a plurality of apertures extending through an external wall portion thereof in communication with the internal cavity, the longitudinal section of the implant member being dimensioned wherein upon positioning the implant member within the intervertebral space with the minor axis extending in the general direction of the axis of the spine, the longitudinal section at least spans the intervertebral space such that the curved external wall portion thereof contacts and supports the adjacent vertebrae, and generally maintains the disc height of the intervertebral disc space during healing.

13. An apparatus for facilitating fusion of adjacent vertebrae comprising an elongated implant member configured and dimensioned for insertion within an intervertebral space defined between adjacent vertebrae, the implant member having a transverse cross-sectional dimension defining a generally curved elliptical configuration along at least a section of the length thereof, the implant member including an internal cavity for accommodating bone growth inducing substances and having a plurality of apertures extending through an external wall portion thereof in communication with the internal cavity, and an external threaded portion for facilitating insertion within the intervertebral space.

14. The apparatus according to claim 13 wherein the implant member includes at least one flute, the one flute being formed in the threaded portion.

15. The apparatus according to claim 13 wherein the implant member includes an entry section having a closed entry end surface.

16. The apparatus according to claim 15 including at least one flute formed in the entry end surface.

17. The apparatus according to claim 13 wherein the implant member includes an entry end section, the entry end section having a transverse cross-sectional dimension defining a generally circular configuration.

18. The apparatus according to claim 13 further including an end cap mountable to the implant member to enclose the internal bore.

19. The apparatus according to claim 17, wherein the implant member includes a trailing end section and an intermediate section between the trailing end section and the entry end section, the entire intermediate section having a transverse cross-sectional dimension defining a generally elliptical configuration.

20. A method for fusion of adjacent vertebrae, comprising the steps of:
    accessing the intervertebral space defined between adjacent vertebrae;
    providing a fusion apparatus including an implant body having an entry end and a trailing end and defining a longitudinal axis, the implant body having a longitudinal section defining a general curved elliptical cross-sectional dimension with a major axis and a minor axis to define a curved outer surface of the longitudinal section of the implant body;
    advancing the entry end of the implant body into the intervertebral space and positioning the implant body such that the curved outer surface of the implant body contacts the adjacent vertebrae; and
    permitting bone ingrowth into contacting surfaces of the implant body to facilitate fusion of the adjacent vertebrae.

21. The method according to claim 20 wherein the step of advancing includes arranging the implant member within the intervertebral space whereby the major axis of the implant member is in general parallel relation with the vertebral end faces of the adjacent vertebrae and the minor axis extends in the general direction of the axis of the spine.

22. The method according to claim 20 including the step of introducing bone growth inducing substances within an internal cavity defined within the implant body whereby the adjacent vertebrae communicates with the bone growth inducing substances to form a solid fusion.

23. The method according to claim 22 wherein the implant body includes an exterior wall portion having apertures extending therethrough wherein the step of permitting bone ingrowth includes permitting bony tissue of the adjacent vertebrae to grow through the apertures to communicate with the bone growth inducing substances.

24. The method according to claim 23 wherein the implant body includes an external threaded portion, wherein the step of positioning includes screwing the implant body into a preformed receiving bore formed into the adjacent vertebrae.

25. The method according to claim 24 wherein the external threaded portion of the implant body includes a cutting thread wherein the step of screwing the implant body includes advancing the implant body within the preformed receiving bore whereby the cutting thread deburrs bone tissue to self-tap the implant body within the preformed receiving bore.

26. A method for fusion of adjacent vertebrae, comprising the steps of:
    accessing the intervertebral space defined between adjacent vertebrae;
    positioning a fusion apparatus into the intervertebral space, the fusion apparatus including an implant body having a longitudinal section defining a general curved elliptical transverse cross-section with a major axis greater than a minor axis, the implant being inserted laterally with respect to the longitudinal axis of the spine and positioned with the minor axis of the longitudinal section extending in the general direction of the longitudinal axis of the spine; and
    permitting bone ingrowth into contacting surfaces of the implant body to facilitate fusion of the adjacent vertebrae.

27. A method for fusion of adjacent vertebrae comprising the steps of:
    accessing the intervertebral space of the lumbar spine defined between adjacent vertebrae; and
    positioning a fusion apparatus into the intervertebral space of the lumbar spine and at an angle of between about 15° and about 45° with respect to the longitudinal axis of the spine and to the right of the great vessels when viewed anteriorly.

28. A method for fusion of adjacent vertebrae, comprising the steps of:
    accessing the intervertebral space defined between adjacent vertebrae;
    providing a fusion apparatus including an implant body having a longitudinal section defining a general curved elliptical transverse cross-section with a major axis greater than a minor axis, the implant body having an external threaded portion;
    positioning the fusion apparatus within the intervertebral space by screwing the implant body into a preformed bore formed in the adjacent vertebrae; and
    permitting bone ingrowth into contacting surfaces of the implant body to facilitate fusion of the adjacent vertebrae.

* * * * *